(12) United States Patent
Takada et al.

(10) Patent No.: US 7,615,237 B1
(45) Date of Patent: Nov. 10, 2009

(54) PERCUTANEOUSLY ABSORBABLE PREPARATIONS

(75) Inventors: Yasunori Takada, Tosu (JP); Koji Tanaka, Tosu (JP); Yasuhiro Ikeura, Tosu (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 1018 days.

(21) Appl. No.: 10/030,825

(22) PCT Filed: Jul. 11, 2000

(86) PCT No.: PCT/JP00/04609

§ 371 (c)(1),
(2), (4) Date: Jan. 11, 2002

(87) PCT Pub. No.: WO01/05381

PCT Pub. Date: Jan. 25, 2001

(30) Foreign Application Priority Data

Jul. 15, 1999 (JP) .................................. 11-201340

(51) Int. Cl.
*A61F 13/00* (2006.01)
*A01N 37/44* (2006.01)
*A01N 47/28* (2006.01)

(52) U.S. Cl. .................. 424/449; 514/887; 514/567

(58) Field of Classification Search ........... 424/448–49, 424/484, 449; 514/947, 887, 567
See application file for complete search history.

(56) References Cited

U.S. PATENT DOCUMENTS

| | | | | |
|---|---|---|---|---|
| 5,120,545 A | * | 6/1992 | Ledger et al. ............... | 424/449 |
| 5,340,572 A | * | 8/1994 | Patel et al. ............... | 424/78.04 |
| 5,773,028 A | * | 6/1998 | Inagi et al. ................ | 424/487 |
| 5,795,916 A | * | 8/1998 | Sekine et al. | |
| 5,866,157 A | | 2/1999 | Higo et al. | |
| 5,968,533 A | * | 10/1999 | Porter et al. ............... | 424/401 |
| 6,262,121 B1 | * | 7/2001 | Kawaji et al. ............... | 514/567 |
| 6,723,337 B1 | | 4/2004 | Song et al. | |

FOREIGN PATENT DOCUMENTS

| | | |
|---|---|---|
| CN | 1171736 A | 1/1998 |
| EP | 0 788 794 A1 | 8/1997 |
| EP | 0 879 597 A1 | 11/1998 |
| JP | 59-164714 | 9/1984 |
| JP | 59-164715 | 9/1984 |
| JP | 61-12621 | 1/1986 |
| JP | 61-260026 | 11/1986 |
| JP | 4-1127 | 1/1992 |
| JP | 04-217925 | 8/1992 |
| JP | 6-205839 | 7/1994 |
| JP | 9-316007 | 9/1997 |
| JP | 10-316560 | 2/1998 |
| JP | 10-114646 | 5/1998 |
| JP | 10-1433 | 6/1998 |
| JP | 10-182450 | 7/1998 |
| JP | 2001-517696 | 10/2001 |
| WO | WO 96/04902 | 2/1996 |
| WO | WO 96/28794 | 8/1997 |

OTHER PUBLICATIONS

Arellano et al. European Journal of Pharmaceutical Sciences, 1998, 7, 129-135.*

* cited by examiner

*Primary Examiner*—Johann R Richter
*Assistant Examiner*—Abigail Fisher
(74) *Attorney, Agent, or Firm*—Edwards Angell Palmer & Dodge LLP; Peter F. Corless; Mark D. Russett

(57) ABSTRACT

Percutaneously absorbable preparations (preferably non-aqueous ones, particularly matrix-type patches or ointment), containing salt-form acidic drugs and characterized by being improved in the percutaneous absorbability of the drug by the incorporation of an addition salt of a basic substance therewith and by being lowly irritant to the skin; and a percutaneous absorption accelerator for salt-form acidic drugs, containing an addition salt of a basic substance.

4 Claims, No Drawings

PERCUTANEOUSLY ABSORBABLE PREPARATIONS

CROSS-REFERENCE TO RELATED APPLICATIONS

This application is the 35 U.S.C. §371 national stage of PCT application PCT/JP2000/04609, filed Jul. 11, 2000, which claims priority to Japanese patent application no. 11-201340/1999, filed Jul. 15, 1999. The contents of these applications are incorporated herein by reference in their entirety.

TECHNICAL FIELD

This invention relates to a percutaneously absorbable preparation wherein percutaneous absorbability of acidic drugs having salt-form is improved. The present invention also relates to a composition for acceleration of percutaneous absorption of acidic drugs having salt-form containing an addition salt compound of a basic substance.

BACKGROUND OF THE INVENTION

As methods for administering drugs, various methods such as oral administration, rectal administration, subcutaneous administration, intravenous administration and the like have been known, and among them, oral administration has been widely employed. However, in the case of oral administration, it has been had disadvantages that drugs readily undergo primary metabolism in liver after absorption and that unnecessarily high concentrations of drugs in blood are transiently observed after administration. Also, lots of side effects such as gastrointestinal hepatic disorder, emetic feeling, anorexia and the like have been reported in oral administration.

Therefore recently, methods by percutaneous administration have been noticed as those which can be anticipated to achieve drug absorption safely and persistently for the purpose of solving such disadvantages of oral administration. The development of percutaneously administering preparations has been already advanced, and the products have been launched in the market.

However, because skin which has a barrier function to prevent invasion of foreign substances into body exerts a stronger barrier function against acidic drugs having salt-form, permeability of drugs is low and sufficient efficacy can not be anticipated. Thus, various attempts have been studied to enhance percutaneous absorption.

For example, Japanese Patent Publication No. 47535/1995 carries out the proposal that percutaneous absorption is enhanced by making a drug be free-form by adding stronger acidic organic acid than acidic drugs. However, the problem in which stability of the drug is lowered and problems such as irritation of skin and reduction of physical property of bases and the like induced by the added organic acid exist due to making the drug be free-form.

Also, ingenuity has been conducted in which percutaneous absorption of drugs is enhanced by combining percutaneous absorption accelerators. For example, the technique in which an absorption accelerator is combined with fatty acid ester (Japanese Patent Laid-Open No. 102656/1990) such as a combination of the absorption accelerator with a lower alkyl amide, for example, ethyl alcohol, isopropyl alcohol, isopropyl palmitate and the like with dimethyl acetamide (U.S. Pat. No. 3,472,931) has been proposed. However, it is a current status that these conventional absorption accelerators and absorption accelerating composition are highly irritative to the skin and thus it is still difficult to say that they are sufficient in safety.

DISCLOSURE OF THE INVENTION

The present invention was carried out to solve the problems of the above conventional art, and aims to provide a percutaneously absorbable preparation which enhances percutaneous absorbability of acidic drugs having salt-form and is lowly irritant to the skin. In particular, the invention aims to provide a matrix-type percutaneously absorbable preparation which enhances percutaneous absorption of an anti-inflammatory drug having salt-form and is lowly irritant to the skin.

As the results of intensive study to solve the problems previously described, the invention has found that percutaneous absorption of anti-inflammatory drugs having salt-form is remarkably improved by combining an addition salt compound of a basic substance in nonaqueous bases containing acidic drugs having salt-form, particularly, by combining an anti-inflammatory drug having salt-form and salts of ammonium compounds in an adhesive basis, has found that percutaneous absorbability of the acidic drug is remarkably improved due to an increase of a partition coefficient to the skin by exchanging ions in the basis between the salt which the acidic drug has and the base which the addition salt compound of the basic substance and so on has, and has been completed based on these findings.

Therefore, the invention provides a percutaneously absorbable preparation in which percutaneous absorbability is improved, characterized in that in the percutaneously absorbable preparation containing an acidic drug having salt-form, an addition salt compound of a basic substance is combined thereto.

The invention provides a percutaneously absorbable preparation containing an acidic drug having salt-form and an addition salt compound of a basic substance in a basis.

The invention also provides a percutaneously absorbable preparation of which percutaneous absorbability is improved containing an acidic drug having salt-form such as an anti-inflammatory drug or a muscular relaxant drug.

Further, the invention relates to a percutaneous absorption accelerator of or a composition for acceleration of percutaneous absorption of an acidic drug having salt-form containing an addition salt compound of a basic substance.

BEST MODE FOR CARRYING OUT THE INVENTION

The invention is described in detail below.

The acidic drug having salt-form of the invention is not specifically limited so long as it is acceptable as medicines. The salts of salt-form in acidic drugs are metals such as alkali metals, alkali earth metals, aluminium and the like, amines such as tromethamine, and the like. Specific drugs include, for example, hypnotic sedative/anti-anxiety medicines (sodium amobarbital, sodium secobarbital, sodium phenobarbital, triclofos sodium dipotassium clorazepate and the like), anti-inflammatory medicines (sodium salicylate, sulpyrine, sodium amfenac, sodium diclofenac, sodium loxoprofen, sodium tolmetin, disodium lobenzarit, ketorolac tromethamine, sodium ketoprofen, sodium ibuprofen, sodium felbinac, sodium flurbiprofen, sodium indomethacin, sodium zomerac, flufenamic acid aluminium, calcium fenoprofen, sodium bromofenac, sodium hydrocortisone succinate, sodium hydrocortisone phosphate, sodium dexamethasone phosphate, sodium dexamethasone metasulfobenzoate, sodium betamethasone phosphate, sodium prednisolone succinate, sodium prednisolone phosphate, sodium methyl prednisolone succinate, sodium prasterone sulfate and the like), muscular relaxant medicines (sodium dantrolene, sodium mivacurium and the like), cardiotonic medicines (sodium bucladesine and the like), diuretic medicines (sodium theobromine, potassium perrhenate, and the like), cardiovascular medicines (sodium ozagrel, sodium pravastatin, calcium nisvastatin and the like), medicines for allergy (sodium cromoglycate, potassium pecirolaste and the like), follicular luteal hormone drugs (estrone sodium sulfate, sodium equilin sulfate and the like), medicines for skin diseases (ciclopirox olamine and the like), blood coagulation inhibitors (potassium warfarin and the like) and medicines for diabetes mellitus (sodium glymidine and the like).

Among them, preferred are anti-inflammatory medicines, muscular relaxant medicines, cardiotonic medicines, cardiovascular medicines and medicines for allergy.

These acidic drugs having salt-form may be used alone or in combination with two or more. A quantity of the acidic drug having salt-form to be combined in the percutaneously absorbable preparation is not specifically limited so long as it is the quantity which exerts its pharmacological effects, and in general, the range from 0.1 to 40% or from 0.5 to 30% by weight is preferable. When the acidic drug in the percutaneously absorbable preparation of the invention is a drug other than an anti-inflammatory drug, the range of its quantity may be from 0.1 to 20% by weight, and preferably from 0.5 to 15% by weight.

The addition salt compound of the basic substance of the invention is a compound which forms a salt by adding the other substance to the basic substance, and the basic substance is preferably Lewis base. Preferred are those which form a salt consisting of a cation and anion moieties by adding a substance having an electron-deficient system such as Lewis acids or a substance capable of forming an electron-deficient system such as organic halides to an electron excess moiety of Lewis base. The anion moiety of the formed addition salt may be organic one of carboxylate and sulfonate and the like, or may be inorganic one of halogen ion, phosphate, carbonate, sulfate and the like, and is not specifically limited so long as it is pharmaceutically acceptable. Also, the addition salt compound of the basic substance of the invention is not limited to water-soluble one, but water-soluble one is preferable.

The preferred addition salt compounds of the basic substance of the invention specifically include salts of ammonium compounds (acid addition salts of ammonia or amines). Salts of the ammonium compounds may be inorganic ones such as ammonium halide, or organic ones such as primary, secondary, tertiary and quaternary ammonium salts. Preferred salts of ammonium compounds include, for example, water-soluble salts of ammonia, dimethylamine, diethylamine, trimethylamine, tetramethyl ammonium, monoethanol amine, diethanol amine, triethanol amine; primary, secondary or tertiary alkyl amines; water-soluble salts of alkanol amine; water-soluble salts of quaternary ammonium; water-soluble salts having pyridinium group(s) and water-soluble salts having pyrrolidinium group(s). Further specifically preferred are ammonium chloride, dimethylamine hydrochloride, diethylamine hydrochloride, 2-ethylhexylamine hydrochloride, n-dodecyl trimethyl ammonium chloride, benzalkonium chloride, tetramethyl ammonium chloride, n-hexadecyl pyridinium chloride, triethanol amine hydrochloride, benzethonium chloride, domiphen bromide, nonylamine hydrochloride, choline hydrochloride, choline phosphate, cetyl pyridinium chloride, methylrosaniline chloride, arginine hydrochloride, lysine hydrochloride, carbachol, oxyquinoline sulfate and the like.

The addition salt compounds of these basic substances may be used alone or in combination with two or more. The quantity of such addition salt compound of the basic substance to be combined in the percutaneously absorbable preparation is not specifically limited so long as it is sufficient to form ion pairs and the like with the acidic drug, and in general, preferred are the range of from 0.5 to 10 fold mole and from 0.5 to 7 fold mole based on the quantity of the acidic drug having salt-form. The combination within this range affords high percutaneous absorbability of the acidic drug. When the quantity to be combined is 0.5 fold mole or less, percutaneous absorbability of the acidic drug is insufficient and thus sufficient efficacy can not be given. When it is more than 10 fold mole, solubility of the addition salt compound of the basic substance in the basis is lowered although efficient percutaneous absorbability of the acidic drug is given, leading to reducing physical property of the preparation and thus it is not preferable. When the acidic drug is an anti-inflammatory drug, the combination up to 7 fold mole is preferable.

The action mechanism of the addition salt compound of the basic substance of the invention is unknown in detail. However, it is believed that a cation moiety of the addition salt compound of the basic substance and a part or entire of a cation moiety of the acidic drug form an ion exchange or complex ionic substance and the resultant ion exchange or complex ionic substance improves percutaneous absorbability.

The percutaneously absorbable preparation of the invention is not limited so long as it is a formulation for percutaneous absorption such as creams, syrups, lotions, ointments, matrix-type patches, but nonaqueous systems are preferable. Especially, nonaqueous ointment, matrix-type patches and the like are preferable. The percutaneously absorbable preparations of the invention include especially matrix-type patches in which an ant-inflammatory drug is used as an active ingredient as one of preferred embodiments.

Therefore, in a more specific preferred embodiment, the invention provides a matrix-type percutaneously absorbable preparation in which percutaneous absorbability is improved, characterized in that salts of ammonium compounds are combined in the matrix-type percutaneously absorbable preparation containing an anti-inflammatory drug having salt-form. That is, the invention provides the matrix-type percutaneously absorbable preparation containing the anti-inflammatory drug having salt-form and salts of ammonium compounds in an adhesive basis layer. It is preferable that the adhesive basis layer of the present invention is composed by combining one or two or more from styrene isoprene-styrene block copolymer, polyisobutylene, and acrylic adhesives and that the anti-inflammatory drug is the acidic drug.

The invention also provides the matrix-type percutaneously absorbable preparation in which percutaneous absorbability is improved, containing the anti-inflammatory drug having salt-form. Further, the invention relates to a percutaneous absorption accelerator or a composition for percutaneous absorption acceleration of the anti-inflammatory drug having salt-form containing salts of ammonium compounds.

The percutaneously absorbable preparation of the present invention can be formulated to the aforementioned formulation by standard methods. Basis ingredients can be appropriately selected for objective formulations.

For example, in ointments, various basis ingredients for ointments can be used as their basis ingredients. Ingredients such as white petrolatum, wax, higher alcohol, hydrocarbon, higher fatty acid, surfactants and the like can be exemplified, and these can be used in combination with two or more.

The matrix-type percutaneously absorbable preparation of this application can be also formulated by standard methods. For example, the objective matrix-type percutaneously absorbable preparation can be produced by mixing/combining required ingredients in an adhesive basis, then applying this on mold-release paper followed by drying and then attaching to a support.

Waxes herein may be any of, for example, plant waxes, animal waxes and mineral waxes, and especially mineral waxes are preferred. The plant waxes include carnauba wax, candelilla wax and the like, the animal waxes include whale wax, bee wax, shellac, lanolin and the like, and the mineral waxes include microcrystalline wax, montan wax, ozokerite, ceresin and the like. Among them, microcrystalline wax is especially preferable. Its quantity to be combined is from 1 to 14% by weight, and preferably from 4 to 10% by weight based on the entire quantity of the ointment. When the quantity to be combined is less than 1% by weight, viscosity of the ointment is difficult to be retained. When the quantity to be combined is more than 14% by weight, it is not preferable because the ointment becomes to be hard and increases dryness.

As higher alcohol, preferred are those of 10 or more of carbon numbers which are liquid or solid. For example, myristate alcohol, isostearyl alcohol, cetyl alcohol, stearyl alcohol, oleyl alcohol, allyl alcohol, 2-octyl decanol, cholesterol, phytosterol, 2-hexyl decanol, behenyl alcohol, lauryl alcohol and the like are included. Among them, stearyl alcohol, oleyl alcohol, 2-octyl decanol and behenyl alcohol are especially preferable. Its quantity to be combined is from 1 to 40% by weight and preferably from 5 to 30% by weight based on the entire quantity of the ointment. When the quantity to be combined is less than 1% by weight, it becomes difficult to retain smoothness for a long time. When it is more than 40% by weight, it is not preferable because viscosity of the ointment is hard to be retained.

Hydrocarbons include, for example, liquid paraffin, light liquid paraffin, light liquid isoparaffin, squalene, squalane, pristane and the like, and among them, liquid paraffin and squalane are especially preferable. The quantity to be combined is from 1 to 30% by weight and preferably from 3 to 25% by weight based on the entire quantity of the ointment. When the quantity to be combined is less than 1% by weight, it becomes difficult to retain smoothness for a long time. When it more than 30% by weight, it is not preferable because surface tackiness is remarkably increased.

Higher fatty acids include, for example, aluminium monostearate, aluminium distearate, aluminium tristearate, zinc stearate, magnesium stearate, zinc laurate, zinc myristate and the like, and among them, aluminium monostearate, aluminium distearate, and aluminium tristearate are especially preferable. The quantity to be combined is from 0.1 to 3% by weight and preferably from 0.5 to 2% by weight based on the entire quantity of the ointment. When the quantity to be combined is less than 0.1% by weight, viscosity of the ointment is hard to be retained. When it is more than 3% by weight, it is not preferable because surface tackiness is remarkably increased.

Surfactant may be either ionic or non-ionic surfactants, but non-ionic surfactants is preferable in terms of skin safety. Examples of such surfactants include sorbitan fatty acid ester (e.g., sorbitan monostearate, sorbitan monoisostearate, sorbitan sesquioleate and the like), glycerine fatty acid ester (e.g., glyceryl monostearate, glyceryl monomyristate and the like), polyglycerine fatty acid ester (e.g., diglyceryl monooleate, diglyceryl monoisostearate, decaglyceryl pentastearate, tetraglyceryl monostearate and the like), polyethylene glycol fatty acid ester (e.g., polyoxyethylene glycol (2) monostearate, polyoxyethylene glycol(2) monooleate and the like), polyoxyethylene alkyl phenyl ether (e.g., polyoxyethylene(2) nonyl phenyl ether, polyoxyethylene(5) nonyl phenyl ether and the like). Among them, polyoxyethylene(2) nonyl phenyl ether of which HLB is 10 or less, decaglyceryl pentastearate, diglyceryl monooleate, diglyceryl monoisostearate, and sorbitan monoisostearate are especially preferable. The quantity to be combined is from 1 to 10% by weight and preferably from 1 to 5% by weight based on the entire quantity of the ointment. When the quantity to be combined is less than 1% by weight, stability for a long time is impaired. When it is 10% or more by weight, it is not preferable because surface tackiness is remarkably increased.

Bases for the matrix-type patch of the percutaneously absorbable preparation of the invention include, for example, styrene-isoprene-styrene block copolymer, styrene-butadiene-styrene block copolymer, styrene-isoprene gum, styrene-butadiene gum, polyisoprene, polyisobutylene, polybutadiene gum, silicone gum, acrylic polymers (copolymer of at least two of 2-ethylhexyl acrylate, vinyl acetate, methacrylate, methoxyethyl acrylate and acrylic acid), natural gum, polyurethane gum and the like. Such bases can be used in combination with two or more. Among them, it is preferable that one or two or more from styrene-isoprene-styrene block copolymer, polyisobutylene, and acrylic adhesives are combined.

More specifically, as styrene-isoprene-styrene block copolymer, one or two or more can be combined from Cariflex TR-1107, TR-1111, TR-1112 or TR-1117 (brand names, Schell Kagaku Co., Ltd.), Quintac 3530 3570C or 3421 (brand names, Zeon Corporation), JSR SIS-5000 or 5002 (Japan Synthetic Rubber Co., Ltd.), and Solprene 428 (brand name, Philip Petroleum Co., Ltd.). The quantity to be combined is from 10 to 40% by weight and preferably from 15 to 35% by weight based on the entire quantity of the patch. This quantity remarkably improves tackiness, adherability to the skin for a long time, percutaneous absorbability of drugs, dispersibility of drugs, pain at peeling, skin fit and the like. When the quantity to be combined is less than 10% by weight, it is not preferable since cohesion and shape retention are reduced. When the quantity to be combined is more than 40% by weight, it is not preferable since cohesion of the basis is increased resulting in reduction of adhesion and unevenness of the ointment body.

As polyisobutylene, one or two or more can be combined from Opanol B-3, B-10, B-15, B-50, B-100, B-200 (brand names, BASF), Vistanex LM-MS, LM-MH, MML-80, LLM-100, LLM-120, LLM-140 (brand names, Exxon Chemical Co., Ltd.), Tetrax 3T, 4T, 5T, 6T (brand names, Nippon Oil Chemical Co., Ltd). The quantity to be combined is from 6 to 40% by weight and preferably from 6.5 to 30% by weight based on the entire quantity of the patch. This quantity remarkably improves tackiness, adherability to the skin for a long time, percutaneous absorbability of drugs, dispersibility of drugs, pain at peeling, skin fit and the like. When the quantity is less than 6% by weight, it is not preferable since tackiness and adherability to the skin for a long time are reduced resulting in increasing pain at peeling and skin fit. When it is more than 40% by weight, it is not preferable since shape retention is reduced and surface tackiness is increased.

Acrylic adhesives are composed of at least two of copolymers from butyl acrylate, 2-ethylhexyl acrylate, vinyl acetate, methacrylate, hydroxyethyl acrylate, glycidyl methacrylate, methoxyethyl acrylate and acrylic acid. Specifically, they are DURO-TAK 87-2097, 87-2194, 87-2196, 87-2287, 87-2516, 87-2852 (brand names, National Starch and Chemical Corporation), Nissetsu KP-77, AS-370 (brand names, Nippon Carbide Industries Co., Inc.) and the like. The quantity to be combined is from 5 to 99% by weight and preferably from 10 to 90% by weight based on the quantity of the matrix-type percutaneously absorbable preparation. This quantity remarkably improves tackiness, adherability to the skin for a long time, percutaneous absorbability of drugs, dispersibility of drugs, pain at peeling, skin fit and the like. When the quantity is less than 5% by weight, it is not preferable since tackiness and adherability to the skin for a long time are reduced resulting in increasing pain at peeling and skin fit.

Tackifiers and plasticizers can be combined in the matrix-type patch as needed.

As tackifiers, for example, rosin ester, hydrogenated rosin ester, maleinized rosin, alicyclic saturated hydrocarbon resin, terpene phenol and the like can be used. Specifically, one or two or more can be combined from Ester gum A, AA-G, H or HP (brand names, Arakawa Chemical Industries Ltd.), Haliester-L, S or P (brand names, Arakawa Chemical Industries Ltd.), Pinecrystal KE-100 (brand name, Arakawa Chemical Industries Ltd.), KE-311 (brand name, Arakawa Chemical Industries Ltd.), Hercoline D (brand name, Chemical Hercules Co., Ltd.), Forral 85 or 105 (brand names, Chemical Hercules Co., Ltd.), Stevelight Ester 7 or 10 (brand name, Chemical Hercules Co., Ltd.), Ventaline 4820 or 4740 (brand name, Chemical Hercules Co., Ltd.), Alcon P-85 or P-100 (brand names, Arakawa Chemical Industries Ltd.) and the like. The quantity to be combined is from 5 to 60% and preferably from 10 to 50% by weight based on the entire quantity of the patch. This quantity remarkably improves tackiness, adherability to the skin for a long time, percutaneous absorbability of drugs, dispersibility of drugs, pain at peeling, skin fit and the like. When the quantity is less than 5% by weight, it is not preferable since tackiness and adherability to the skin for a long time are reduced. When it is more than 60% by weight, it is not preferable since percutaneous absorbability of drugs and shape retention are reduced resulting in increasing pain at peeling, skin fit, surface tackiness and so on.

As plasticizers, one or two or more can be combined from petroleum oils (e.g., paraffin process oils, naphthene process oils, aromatic process oils and the like), squalane, squalene, plant oils (e.g., olive oil, Camellia japonica oil, castor oil, tall oil, peanut oil), dibasic esters (e.g., dibutyl phthalate, dioctyl phthalate and the like), liquid gum (e.g., polybutene, liquid isoprene gum and the like) and the like. Among them, liquid paraffin and liquid polybutene are especially preferable. The quantity to be combined is from 7 to 70% and preferably from 10 to 60% by weight based on the entire quantity of the patch. This quantity remarkably improves tackiness, adherability to the skin for a long time, percutaneous absorbability of drugs, dispersibility of drugs, pain at peeling, skin fit and the like. When the quantity is less than 7% by weight, it is not preferable since tackiness, percutaneous absorbability of drugs and dispersibility of drugs are reduced. When it is more than 70% by weight, it is not preferable since cohesion and shape retention are reduced resulting in increasing pain at peeling, surface tackiness and so on.

Into the matrix-type percutaneously absorbable preparation of the invention, further anti-oxidants (e.g., ascorbic acid, propyl gallate, butylhydroxy anisole, dibutylhydroxy toluene [BHT], nordi hydroguaiaretic acid, tocopherol, tocopherol acetate and the like), UV absorbents (e.g., para-amino benzoate, para-amino benzoate ester, para-dimethyl amino benzoate amyl, salicylic ester, methyl anthranilate, umbeliferone, esclin, benzyl cinnamate, cinoxate, guaiazulene, urocanic acid, 2-(2-hydroxy-5-methylphenyl) benzotriazole, 4-methoxy benzophenone, 2-hydroxy-4-methoxy benzophenone, octabenzene, dioxybenzone, dihydroxy dimethoxy benzophenone, sulinbenzone, benzoresorcinol, octyl dimethyl para-amino benzoate, ethylhexyl para-methoxy cinnamate and the like), antibacterial agents (e.g., para-oxy benzoate ester, benzoic acid, benzoate, sorbic acid, sorbate, dehydroacetate, 4-isopropyl-3-methylphenol, 2-isopropyl-5-methylphenol, hinokitiol, cresol, 2,4,4-trichloro-2'-hydroxy-diphenyl ether, 3,4,4'-trichlorocarbanide, chloro butanol and the like), fillers (e.g., aluminium hydroxide, hydrated aluminium silicate, kaolin, titanium oxide, talc, zinc oxide, hydrated silica, magnesium carbonate, calcium hydrogen phosphate, magnesium silicate, diatomite, silicic anhydride, bentonite, sodium stearate, calcium stearate, potassium stearate, magnesium stearate, zinc stearate and the like), antihistamic agents (e.g., isopentyl chloride, diphenhydramine hydrochloride, isoproheptine hydrochloride, diphenylpyrraline hydrochloride, ciproheptazine hydrochloride, triprolysine hydrochloride, promethazine hydrochloride, homochlorocyclidine hydrochloride, alimemazine tartrate, diphenhydramine tannate, theoclate diphenylpyrraline, clemastine fumarate, chloropheniramine maleate, dimethindene maleate, metaquitazine, and the like), refrigerants, fragrances and the like can be combined as needed.

The examples are shown below and described more specifically, but the invention is not limited to these examples and can be changed variously. The parts described in Examples and Comparative Examples represent parts by weight.

EXAMPLES

Example 1

Styrene-isoprene-styrene block copolymer
(brand name: Cariflex TR-1107) 30.0 parts
Liquid paraffin 42.0 parts
Alicyclic saturated hydrocarbon resin
(brand name: Alcon P-85) 20.0 parts
Sodium amfenac 5.0 parts
Diethylamine hydrochloride 3.0 parts All of these ingredients were melted with heat and then applied on the mold-release paper at a thickness of 100 μm followed by attaching with polyester supports to afford the percutaneously absorbable preparation of the invention.

Example 2

Acrylate 2-ethylhexyl ester 50.0 parts
Acrylate methoxyethyl ester 27.0 parts
Vinyl acetate 14.7 parts
Azobisisobutyronitrile 0.3 parts
Sodium amfenac 5.0 parts
Dimethylamine hydrochloride 3.0 parts Acrylate 2-ethylhexyl ester, acrylate methoxyethyl ester, vinyl acetate and azobisisobutyronitrile were placed in a reaction vessel, and the polymerization was started with elevating a temperature at 65° C. in a nitrogen atmosphere. Dripping 120 parts of ethyl acetate, the reaction was continued with control of the temperature for 10 hours, and further aged at 80° C. for 2 hours to yield a copolymer solution. Sodium amfenac and dimethylamine hydrochloride were added to and mixed with the resulting copolymer solution, and then applied on the mold-release paper at a thickness after dry of 100 μm. After dry, it was attached with polyester supports to afford the percutaneously absorbable preparation of the invention.

Example 3

Styrene-isoprene-styrene block copolymer
(brand name: Cariflex TR-1111) 25.0 parts
Liquid paraffin 42.0 parts
Rosin resin
(brand name: Forral 85) 15.0 parts
Polyisobutylene
(brand name: Opanol B-100) 10.0 parts
Sodium amfenac 5.0 parts
Nonylamine hydrochloride 3.0 parts All of these ingredients were melted in a toluene solvent and applied on the mold release paper at a thickness after dry of 100 μm. After dry, it was attached with polyester supports to afford the percutaneously absorbable preparation of the invention.

Example 4

Styrene-isoprene-styrene block copolymer
(brand name: JSR SIS-5000) 20.0 parts
Liquid paraffin 41.0 parts
Alicyclic saturated hydrocarbon resin
(brand name: Alcon P-100) 20.0 parts
Polyisobutylene
(brand name: Vistanex MML-140) 15.0 parts
Sodium diclofenac 3.0 parts
Ammonium chloride 1.0 parts All of these ingredients were melted with heat and then applied on the mold release paper at a thickness of 100 μm followed by attaching with polyester supports to afford the percutaneously absorbable preparation of the invention.

Example 5

Acrylate 2-ethylhexyl ester 50.0 parts
Acrylate methoxyethyl ester 30.0 parts
Vinyl acetate 14.7 parts
Azobisisobutyronitrile 0.3 parts
Sodium diclofenac 3.0 parts
Nonylamine hydrochloride 2.0 parts Acrylate 2-ethylhexyl ester, acrylate methoxyethyl ester, vinyl acetate and azobisisobutyronitrile were placed in a reaction vessel, and the polymerization was started with elevating a temperature at 65° C. in a nitrogen atmosphere. Dripping 120 parts of ethyl acetate, the reaction was continued with control of the temperature for 10 hours, and further aged at 80° C. for 2 hours to yield a copolymer solution. Sodium diclofenac and nonylamine hydrochloride were added to and mixed with the resulting copolymer solution, and then applied on the mold-release paper at a thickness after dry of 100 μm. After dry, it was attached with polyester supports to afford the percutaneously absorbable preparation of the invention.

Example 6

Styrene-isoprene-styrene block copolymer
(brand name: Cariflex TR-1117) 35.0 parts
Liquid paraffin 45.5 parts
Rosin resin
(brand name: Pinecrystal KE-100) 15.0 parts
Sodium diclofenac 3.0 parts
Diethylamine hydrochloride 1.5 parts All of these ingredients were melted in a toluene solvent and applied on the mold-release paper at a thickness after dry of 100 μm. After dry, it was attached with polyester supports to afford the percutaneously absorbable preparation of the invention.

Example 7

Styrene-isoprene-styrene block copolymer
(brand name: Quintac 3530) 30.0 parts
Liquid paraffin 39.0 parts
Rosin resin
(brand name: Ester Gum H) 20.0 parts
Sodium loxoprofene 5.0 parts
n-Dodecyl trimethyl ammonium chloride 6.0 parts All of these ingredients were melted with heat and then applied on the mold-release paper at a thickness of 100 μm followed by attaching with polyester supports to afford the percutaneously absorbable preparation of the invention.

Example 8

Styrene-isoprene-styrene block copolymer
(brand name: Cariflex TR-1112) 15.0 parts
Liquid paraffin 33.0 parts
Alicyclic saturated hydrocarbon resin
(brand name: Alcon P-100) 25.0 parts
Polyisobutylene
(brand name: Opanol B-100) 20.0 parts
Sodium loxoprofene 5.0 parts
Ammonium chloride 2.0 parts All of these ingredients were melted in a toluene solvent and applied on the mold-release paper at a thickness after dry of 100 μm. After dry, it was attached with polyester supports to afford the percutaneously absorbable preparation of the invention.

Example 9

Acrylate 2-ethylhexyl ester 43.0 parts
Acrylate methoxyethyl ester 35.0 parts
Vinyl acetate 9.7 parts
Azobisisobutyronitrile 0.3 parts
Sodium loxoprofene 5.0 parts
Benzalkonium chloride 7.0 parts Acrylate 2-ethylhexyl ester, acrylate methoxyethyl ester, vinyl acetate and azobisisobutyronitrile were placed in a reaction vessel, and the polymerization was started with elevating a temperature at 65° C. in a nitrogen atmosphere. Dripping 120 parts of ethyl acetate, the reaction was continued with control of the temperature for 10 hours, and further aged at 80° C. for 2 hours to yield a copolymer solution. Sodium loxoprofene and Benzalkonium chloride were added to and mixed with the resulting copolymer solution, and then applied on the mold-release paper at a thickness after dry of 100 μm. After dry, it was attached with polyester supports to afford the percutaneously absorbable preparation of the invention.

Example 10

Styrene-isoprene-styrene block copolymer
(brand name: JSR SIS-5002) 20.0 parts
Liquid paraffin 47.0 parts
Rosin resin
(brand name: Stevelight Ester 7) 10.0 parts Polyisobutylene
(brand name: Vistanex LM-MH) 20.0 parts
Ketorolactromethamine 2.0 parts
Dimethylamine hydrochloride 1.0 parts All of these ingredients were melted with heat and then applied on the mold-release paper at a thickness of 100 μm followed by attaching with polyester supports to afford the percutaneously absorbable preparation of the invention.

Example 11

Styrene-isoprene-styrene block copolymer
(brand name: Quintac 3421) 15.0 parts
Liquid paraffin 40.0 parts
Rosin resin
(brand name: KE-311) 10.0 parts
Polyisobutylene
(brand name: Opanol B-50) 30.0 parts
Ketorolactromethamine 2.0 parts
n-Dodecyl trimethyl ammonium chloride 3.0 parts All of these ingredients were melted in a toluene solvent and applied on the mold-release paper at a thickness after dry of 100 μm. After dry, it was attached with polyester supports to afford the percutaneously absorbable preparation of the invention.

Example 12

Acrylate 2-ethylhexyl ester 55.0 parts
Acrylate methoxyethyl ester 26.0 parts
Vinyl acetate 14.7 parts
Azobisisobutyronitrile 0.3 parts
Ketorolactromethamine 2.0 parts
2-ethylhexylamine hydrochloride 2.0 parts Acrylate 2-ethylhexyl ester, acrylate methoxyethyl ester, vinyl acetate and azobisisobutyronitrile were placed in a reaction vessel, and the polymerization was started with elevating a temperature at 65° C. in a nitrogen atmosphere. Dripping 120 parts of ethyl acetate, the reaction was continued with control of the temperature for 10 hours, and further aged at 80° C. for 2 hours to yield a copolymer solution. Ketorolactromethamine and 2-ethylhexylamine hydrochloride were added to and mixed with the resulting copolymer solution, and then applied on the mold-release paper at a thickness after dry of 100 μm. After dry, it was attached with polyester supports to afford the percutaneously absorbable preparation of the invention.

Example 13

Styrene-isoprene-styrene block copolymer
(brand name: Cariflex TR-1107) 25.0 parts
Liquid paraffin 43.0 parts
Rosin resin
(brand name: KE-311) 7.0 parts
Polyisobutylene
(brand name: Tetrax 5T) 13.0 parts
Sodium bucladesine 7.0 parts
n-Hexadecyl pyridinium chloride 5.0 parts All of these ingredients were melted in a toluene solvent and applied on the mold-release paper at a thickness after dry of 100 μm. After dry, it was attached with polyester supports to afford the percutaneously absorbable preparation of the invention.

Example 14

Acrylate 2-ethylhexyl ester 50.0 parts
Acrylate methoxyethyl ester 23.0 parts
Vinyl acetate 14.7 parts
Azobisisobutyronitrile 0.3 parts
Sodium bucladesine 7.0 parts
2-Ethylhexylamine hydrochloride 5.0 parts Acrylate 2-ethylhexyl ester, acrylate methoxyethyl ester, vinyl acetate and azobisisobutyronitrile were placed in a reaction vessel, and the polymerization was started with elevating a temperature at 65° C. in a nitrogen atmosphere. Dripping 120 parts of ethyl acetate, the reaction was continued with control of the temperature for 10 hours, and further aged at 80° C. for 2 hours to yield a copolymer solution. Sodium bucladesine and 2-ethylhexylamine hydrochloride were added to and mixed with the resulting copolymer solution, and then applied on the mold-release paper at a thickness after dry of 100 μm. After dry, it was attached with polyester supports to afford the percutaneously absorbable preparation of the invention.

Example 15

Styrene-isoprene-styrene block copolymer
(brand name: Quintac 3570C) 20.0 parts
Liquid paraffin 42.5 parts
Rosin resin
(brand name: Pentaline 4820) 20.0 parts
Polyisobutylene
(brand name: Vistanex LM-MS) 15.0 parts
Sodium ozagrel 2.0 parts
Tetramethyl ammonium chloride 0.5 parts All of these ingredients were melted in a toluene solvent and applied on the mold-release paper at a thickness after dry of 100 μm. After dry, it was attached with polyester supports to afford the percutaneously absorbable preparation of the invention.

Example 16

Acrylate 2-ethylhexyl ester 55.0 parts
Acrylate methoxyethyl ester 30.0 parts
Vinyl acetate 11.7 parts
Azobisisobutyronitrile 0.3 parts
Sodium ozagrel 2.0 parts
Diethylamine hydrochloride 1.0 parts Acrylate 2-ethylhexyl ester, acrylate methoxyethyl ester, vinyl acetate and azobisisobutyronitrile were placed in a reaction vessel, and the polymerization was started with elevating a temperature at 65° C. in a nitrogen atmosphere. Dripping 120 parts of ethyl acetate, the reaction was continued with control of the temperature for 10 hours, and further aged at 80° C. for 2 hours to yield a copolymer solution. Sodium ozagrel and diethylamine hydrochloride were added to and mixed with the resulting copolymer solution, and then applied on the mold-release paper at a thickness after dry of 100 μm. After dry, it was attached with polyester supports to afford the percutaneously absorbable preparation of the invention.

Example 17

Styrene-isoprene-styrene block copolymer
(brand name: JSR SIS-5000) 30.0 parts

Liquid paraffin 40.0 parts
Alicyclic saturated hydrocarbon resin
(brand name: Alcon P-100) 15.0 parts
Polyisobutylene
(brand name: Opanol B-100) 10.0 parts
Sodium cromoglycate 4.0 parts
Ammonium chloride 1.0 parts All of these ingredients were melted in a toluene solvent and applied on the mold-release paper at a thickness after dry of 100 μm. After dry, it was attached with polyester supports to afford the percutaneously absorbable preparation of the invention.

Example 18

Acrylate 2-ethylhexyl ester 52.0 parts
Acrylate methoxyethyl ester 27.0 parts
Vinyl acetate 14.7 parts
Azobisisobutyronitrile 0.3 parts
Sodium cromoglycate 4.0 parts
Dimethylamine hydrochloride 2.0 parts
Acrylate 2-ethylhexyl ester, acrylate methoxyethyl ester, vinyl acetate and azobisisobutyronitrile were placed in a reaction vessel, and the polymerization was started with elevating a temperature at 65° C. in a nitrogen atmosphere. Dripping 120 parts of ethyl acetate, the reaction was continued with control of the temperature for 10 hours, and further aged at 80° C. for 2 hours to yield a copolymer solution. Sodium cromoglycate and dimethylamine hydrochloride were added to and mixed with the resulting copolymer solution, and then applied on the mold-release paper at a thickness after dry of 100 μm. After dry, it was attached with polyester supports to afford the percutaneously absorbable preparation of the invention.

Example 19

Diglyceryl monostearate 5.0 parts
Behenyl alcohol 5.0 parts
Aluminium monostearate 1.0 parts
Liquid paraffin 8.0 parts
Squalane 4.0 parts
White petrolatum 73.0 parts
Sodium diclofenac 3.0 parts
Ammonium chloride 1.0 parts
All of these ingredients were mixed homogenously at 90 to 95° C., and then cooled to 35° C. with stirring to afford a white and glossy ointment.

Example 20

Diglyceryl monostearate 5.0 parts
Behenyl alcohol 5.0 parts
Aluminium monostearate 1.0 parts
Liquid paraffin 8.0 parts
Squalane 4.0 parts
White petrolatum 70.0 parts
Sodium loxoprofene 5.0 parts
Ammonium chloride 2.0 parts
All of these ingredients were mixed homogenously at 90 to 95° C., and then cooled to 35° C. with stirring to afford a white and glossy ointment.

Example 21

Diglyceryl monostearate 5.0 parts
Behenyl alcohol 5.0 parts
Aluminium monostearate 1.0 parts
Liquid paraffin 8.0 parts
Squalane 4.0 parts
White petrolatum 72.0 parts
Ketorolactromethamine 2.0 parts
n-Dodecyl trimethyl ammonium chloride 3.0 parts
All of these ingredients were mixed homogenously at 90 to 95° C., and then cooled to 35° C. with stirring to afford a white and glossy ointment.

Example 22

Styrene-isoprene-styrene block copolymer
(brand name: Solprene 428) 30.0 parts
Liquid paraffin 44.0 parts
Alicyclic saturated hydrocarbon resin
(brand name: Alcon P-85) 20.0 parts
Sodium dantrolene 1.0 parts
Domiphen bromide 5.0 parts
All of these ingredients were melted with heat and then applied on the mold-release paper at a thickness of 100 μm followed by attaching with polyester supports to afford the percutaneously absorbable preparation of the invention.

Example 23

Acrylate 2-ethylhexyl ester 55.0 parts
Acrylate methoxyethyl ester 30.0 parts
Vinyl acetate 10.7 parts
Azobisisobutyronitrile 0.3 parts
Sodium dantrolene 1.0 parts
n-Hexadecyl pyridinium chloride 3.0 parts
Acrylate 2-ethylhexyl ester, acrylate methoxyethyl ester, vinyl acetate and azobisisobutyronitrile were placed in a reaction vessel, and the polymerization was started with elevating a temperature at 65° C. in a nitrogen atmosphere. Dripping 120 parts of ethyl acetate, the reaction was continued with control of the temperature for 10 hours, and further aged at 80° C. for 2 hours to yield a copolymer solution. Sodium dantrolene and n-hexadecyl pyridinium chloride were added to and mixed with the resulting copolymer solution, and then applied on the mold-release paper at a thickness after dry of 100 μm. After dry, it was attached with polyester supports to afford the percutaneously absorbable preparation of the invention.

Example 24

Styrene-isoprene-styrene block copolymer
(brand name: Cariflex TR-1117) 20.0 parts
Liquid paraffin 48.4 parts
Alicyclic saturated hydrocarbon resin
(brand name: Alcon P-100) 20.0 parts
Polyisobutylene
(brand name: Vistanex LM-MH) 10.0 parts
Sodium dantrolene 1.0 parts
Benzalkonium chloride 0.6 parts
All of these ingredients were melted in a toluene solvent and applied on the mold-release paper at a thickness after dry of 100 μm. After dry, it was attached with polyester supports to afford the percutaneously absorbable preparation of the invention.

Example 25

Styrene-isoprene-styrene block copolymer
(brand name: Cariflex TR-1117) 20.0 parts
Liquid paraffin 47.0 parts Alicyclic saturated hydrocarbon resin
(brand name: Alcon P-100) 20.0 parts
Polyisobutylene
(brand name: Vistanex LM-MH) 10.0 parts
Sodium dantrolene 1.0 parts
Benzalkonium chloride 2.0 parts All of these ingredients were melted in a toluene solvent and applied on the mold-release paper at a thickness after dry of 100 μm. After dry, it was attached with polyester supports to afford the percutaneously absorbable preparation of the invention.

Example 26

Styrene-isoprene-styrene block copolymer
(brand name: Cariflex TR-1117) 20.0 parts
Liquid paraffin 44.0 parts
Alicyclic saturated hydrocarbon resin
(brand name: Alcon P-100) 20.0 parts
Polyisobutylene
(brand name: Vistanex LM-MH) 10.0 parts
Sodium dantrolene 1.0 parts
Benzalkonium chloride 5.0 parts All of these ingredients were melted in a toluene solvent and applied on the mold-release paper at a thickness after dry of 100 μm. After dry, it was attached with polyester supports to afford the percutaneously absorbable preparation of the invention.

Example 27

Styrene-isoprene-styrene block copolymer
(brand name: Cariflex TR-1117) 20.0 parts
Liquid paraffin 39.0 parts
Alicyclic saturated hydrocarbon resin
(brand name: Alcon P-100) 20.0 parts
Polyisobutylene
(brand name: Vistanex LM-MH) 10.0 parts
Sodium dantrolene 1.0 parts
Benzalkonium chloride 10.0 parts All of these ingredients were melted in a toluene solvent and applied on the mold-release paper at a thickness after dry of 100 μm. After dry, it was attached with polyester supports to afford the percutaneously absorbable preparation of the invention.

Comparative Example 1

The patch was manufactured by way of trial by the same composition and process for production as those in Example 1, except that diethylamine hydrochloride which is the addition salt compound of the basic substance was not combined.

Comparative Example 2

The patch was manufactured by way of trial by the same composition and process for production as those in Example 2, except that dimethylamine hydrochloride which is the addition salt compound of the basic substance was not combined.

Comparative Example 3

The patch was manufactured by way of trial by the same composition and process for production as those in Example 3, except that nonylamine hydrochloride which is the addition salt compound of the basic substance was not combined.

Comparative Example 4

The patch was manufactured by way of trial by the same composition and process for production as those in Example 4, except that ammonium chloride which is the addition salt compound of the basic substance was not combined.

Comparative Example 5

The patch was manufactured by way of trial by the same composition and process for production as those in Example 5, except that nonylamine hydrochloride which is the addition salt compound of the basic substance was not combined.

Comparative Example 6

The patch was manufactured by way of trial by the same composition and process for production as those in Example 6, except that diethylamine hydrochloride which is the addition salt compound of the basic substance was not combined.

Comparative Example 7

The patch was manufactured by way of trial by the same composition and process for production as those in Example 7, except that n-dodecyl trimethyl ammonium chloride which is the addition salt compound of the basic substance was not combined.

Comparative Example 8

The patch was manufactured by way of trial by the same composition and process for production as those in Example 8, except that ammonium chloride which is the addition salt compound of the basic substance was not combined.

Comparative Example 9

The patch was manufactured by way of trial by the same composition and process for production as those in Example 9, except that benzalkonium chloride which is the addition salt compound of the basic substance was not combined.

Comparative Example 10

The patch was manufactured by way of trial by the same composition and process for production as those in Example 10, except that diethylamine hydrochloride which is the addition salt compound of the basic substance was not combined.

Comparative Example 11

The patch was manufactured by way of trial by the same composition and process for production as those in Example 11, except that n-dodecyl trimethyl ammonium chloride which is the addition salt compound of the basic substance was not combined.

Comparative Example 12

The patch was manufactured by way of trial by the same composition and process for production as those in Example 12, except that 2-ethylhexylamine hydrochloride which is the addition salt compound of the basic substance was not combined.

Comparative Example 13

The patch was manufactured by way of trial by the same composition and process for production as those in Example 13, except that n-hexadecyl pyridinium chloride which is the addition salt compound of the basic substance was not combined.

Comparative Example 14

The patch was manufactured by way of trial by the same composition and process for production as those in Example 14, except that 2-ethylhexylamine hydrochloride which is the addition salt compound of the basic substance was not combined.

Comparative Example 15

The patch was manufactured by way of trial by the same composition and process for production as those in Example 15, except that tetramethyl ammonium chloride which is the addition salt compound of the basic substance was not combined.

Comparative Example 16

The patch was manufactured by way of trial by the same composition and process for production as those in Example 16, except that diethylamine hydrochloride which is the addition salt compound of the basic substance was not combined.

Comparative Example 17

The patch was manufactured by way of trial by the same composition and process for production as those in Example 17, except that ammonium chloride which is the addition salt compound of the basic substance was not combined.

Comparative Example 18

The patch was manufactured by way of trial by the same composition and process for production as those in Example 18, except that diethylamine hydrochloride which is the addition salt compound of the basic substance was not combined.

Comparative Example 19

The ointment was manufactured by way of trial by the same composition and process for production as those in Example 19, except that ammonium chloride which is the addition salt compound of the basic substance was not combined.

Comparative Example 20

The ointment was manufactured by way of trial by the same composition and process for production as those in Example 20, except that ammonium chloride which is the addition salt compound of the basic substance was not combined.

Comparative Example 21

The ointment was manufactured by way of trial by the same composition and process for production as those in Example 21, except that n-dodecyl trimethyl ammonium chloride which is the addition salt compound of the basic substance was not combined.

Comparative Example 22

The patch was manufactured by way of trial by the same composition and process for production as those in Example 22, except that domiphen bromide which is the addition salt compound of the basic substance was not combined.

Comparative Example 23

The patch was manufactured by way of trial by the same composition and process for production as those in Example 23, except that n-hexadecyl pyridinium chloride which is the addition salt compound of the basic substance was not combined.

Comparative Example 24

The patch was manufactured by way of trial by the same composition and process for production as those in Example 24, except that benzalkonium chloride which is the addition salt compound of the basic substance was not combined.

Comparative Example 25

Styrene-isoprene-styrene block copolymer
(brand name: Cariflex TR-1117) 20.0 parts
Liquid paraffin 48.8 parts
Alicyclic saturated hydrocarbon resin
(brand name: Alcon P-100) 20.0 parts
Polyisobutylene
(brand name: Vistanex LM-MH) 10.0 parts
Sodium dantrolene 1.0 parts
Benzalkonium chloride 0.2 parts All of these ingredients were melted in a toluene solvent and applied on the mold-release paper at a thickness after dry of 100 μm. After dry, it was attached with polyester supports to afford the percutaneously absorbable preparation of the invention.

Comparative Example 26

Styrene-isoprene-styrene block copolymer
(brand name: Cariflex TR-1117) 20.0 parts
Liquid paraffin 36.0 parts
Alicyclic saturated hydrocarbon resin
(brand name: Alcon P-100) 20.0 parts
Polyisobutylene
(brand name: Vistanex LM-MH) 10.0 parts
Sodium dantrolene 1.0 parts
Benzalkonium chloride 13.0 parts All of these ingredients were melted in a toluene solvent and applied on the mold-release paper at a thickness after dry of 100 μm. After dry, it was attached with polyester supports to afford the percutaneously absorbable preparation of the invention.

Test Example 1

In Vitro Skin Permeability Test

Pieces of dorsal skin in hairless mice (8 weeks of age, females) were excised and fat layers on the side of dermis were carefully removed. Water at 37° C. was set in a flow through cell which circulated periphery of a receptor layer such that the side of dermis became to be the receptor layer. The percutaneously absorbable preparation of the example or the comparative example was patched or applied on the side of a corneal layer, and phosphate buffer at pH 7.4 was used on the side of the receptor layer. Then sampling was done at a rate of 1 ml/h every one hour up to 24 hours. For the solution obtained every one hour, its quantity was accurately measured, and a concentration of a drug was determined by a high performance liquid chromatography method. A permeable rate per hour was calculated and a skin permeable rate in a steady state was determined according to the following formula.

Skin permeable rate ($\mu g/cm^2/hr$)=[Sample concentration ($\mu g/ml$)×Fluid flow (ml)]/Application area of preparation ($cm^2$)

The results are shown in Table 1.

TABLE 1

|  | skin permeable rate ($\mu g/cm^2/hr$) |
|---|---|
| Example 1 | 6.82 |
| Comparative Example 1 | 0.85 |
| Example 2 | 3.22 |
| Comparative Example 2 | 0.36 |
| Example 3 | 7.32 |
| Comparative Example 3 | 1.11 |
| Example 4 | 9.51 |
| Comparative Example 4 | 1.34 |
| Example 5 | 5.52 |
| Comparative Example 5 | 0.88 |
| Example 6 | 7.56 |
| Comparative Example 6 | 0.66 |
| Example 7 | 8.33 |
| Comparative Example 7 | 1.36 |
| Example 8 | 15.68 |
| Comparative Example 8 | 1.58 |
| Example 9 | 4.62 |
| Comparative Example 9 | 0.31 |
| Example 10 | 8.69 |
| Comparative Example 10 | 0.31 |
| Example 11 | 9.97 |
| Comparative Example 11 | 0.46 |
| Example 12 | 2.52 |
| Comparative Example 12 | 0.15 |
| Example 13 | 2.06 |
| Comparative Example 13 | 0.08 |
| Example 14 | 1.56 |
| Comparative Example 14 | 0.06 |
| Example 15 | 2.33 |
| Comparative Example 15 | 0.16 |
| Example 16 | 1.57 |
| Comparative Example 16 | 0.09 |
| Example 17 | 3.22 |
| Comparative Example 17 | 0.25 |
| Example 18 | 1.88 |
| Comparative Example 18 | 0.19 |
| Example 19 | 6.24 |
| Comparative Example 19 | 1.30 |
| Example 20 | 10.30 |
| Comparative Example 20 | 2.20 |
| Example 21 | 5.83 |
| Comparative Example 21 | 1.05 |
| Example 22 | 0.82 |
| Comparative Example 22 | 0.06 |
| Example 23 | 0.41 |
| Comparative Example 23 | 0.02 |
| Example 24 | 0.40 |
| Example 25 | 0.61 |
| Example 26 | 0.88 |
| Example 27 | 1.02 |
| Comparative Example 24 | 0.05 |
| Comparative Example 25 | 0.10 |
| Comparative Example 26 | 1.01 |

From these results, it is shown that percutaneous absorption is remarkably increased in the percutaneously absorbable preparations containing the addition salt compound of the basic substance of the invention compared to those without the addition salt compound. It is also shown that it is not preferable that its quantity to be combined is excessively much or less though percutaneous absorption is improved by combining the addition salt compound of the basic substance (see Comparative Examples 25 and 26).

Example 28

Styrene-isoprene-styrene block copolymer
(brand name: Cariflex TR-1107) 30.0 parts
Liquid paraffin 42.0 parts
Alicyclic saturated hydrocarbon resin
(brand name: Alcon P-85) 20.0 parts
Sodium diclofenac 5.0 parts
Diethylamine hydrochloride 3.0 parts All of these ingredients were added to toluene, adhesive base ingredients were dissolved, and the mixture was then applied on the mold-release paper at a thickness after dry of 100 μm. After dry, it was attached with polyester supports to afford the matrix-type percutaneously absorbable preparation of the invention.

Example 29

Acrylic adhesive
(brand name: DURO-TAK 87-2194) 76.0 parts
Sodium diclofenac 20.0 parts
Diethylamine hydrochloride 4.0 parts Sodium diclofenac and diethylamine hydrochloride were dissolved in an acrylic adhesive solution, and then applied on the mold-release paper at a thickness after dry of 50 μm. After dry, it was attached with polyester supports to afford the matrix-type percutaneously absorbable preparation of the invention.

Example 30

Styrene-isoprene-styrene block copolymer
(brand name: Cariflex TR-1111) 25.0 parts
Liquid paraffin 32.0 parts
Rosin resin
(brand name: Forral 85) 20.0 parts
Polyisobutylene
(brand name: Opanol B-100) 15.0 parts
Sodium diclofenac 5.0 parts
Ammonium chloride 3.0 parts All of these ingredients were added to toluene, adhesive base ingredients were dissolved and then the mixture was applied on the mold-release paper at a thickness after dry of 100 μm. After dry, it was attached with polyester supports to afford the matrix-type percutaneously absorbable preparation of the invention.

Example 31

Styrene-isoprene-styrene block copolymer
(brand name: JSR SIS-5000) 30.0 parts
Acrylic adhesive
(brand name: DURO-TAK 87-2516) 57.0 parts
Sodium diclofenac 10.0 parts
Ammonium chloride 3.0 parts Styrene-isoprene-styrene block copolymer, sodium diclofenac and ammonium chloride were dissolved in an acrylic adhesive solution, and then applied on the mold-release paper at a thickness after dry of 50 μm. After dry, it was attached with polyester supports to afford the matrix-type percutaneously absorbable preparation of the invention.

Example 32

Polyisobutylene
(brand name: Vistanex LM-MS) 30.0 parts
Acrylic adhesive
(brand name: DURO-TAK 87-2516) 56.0 parts
Sodium diclofenac 10.0 parts
Diethylamine hydrochloride 4.0 parts Sodium diclofenac and diethylamine hydrochloride were dissolved in an acrylic adhesive solution, to which a solution where polyisobutylene was dissolved in toluene was added, and mixed homogenously. Then, the solution was applied on the mold-release paper at a thickness after dry of 50 μm. After dry, it was attached with polyester supports to afford the matrix-type percutaneously absorbable preparation of the invention.

Example 33

Styrene-isoprene-styrene block copolymer
(brand name: Cariflex TR-1107) 35.0 parts
Liquid paraffin 44.0 parts
Rosin resin
(brand name: KE-311) 15.0 parts
Ketorolactromethamine 2.0 parts
n-Dodecyl trimethyl ammonium chloride 4.0 parts All of these ingredients were added to toluene, adhesive base ingredients were dissolved and then applied on the mold-release paper at a thickness after dry of 100 μm. After dry, it was attached with polyester supports to afford the matrix-type percutaneously absorbable preparation of the invention.

Example 34

Acrylic adhesive
(brand name: Nissetsu KP-77) 55.0 parts
Ketorolactromethamine 25.0 parts
2-Ethylhexylamine hydrochloride 20.0 parts Ketorolactromethamine and diethylamine hydrochloride were dissolved in an acrylic adhesive solution, and then applied on the mold-release paper at a thickness after dry of 50 μm. After dry, it was attached with polyester supports to afford the matrix-type percutaneously absorbable preparation of the invention.

Example 35

Styrene-isoprene-styrene block copolymer
(brand name: cariflex TR-1111) 10.0 parts
Liquid paraffin 39.0 parts
Alicyclic saturated hydrocarbon resin
(brand name: Alcon P-100) 20.0 parts
Polyisobutylene
(brand name: Opanol B-100) 20.0 parts
Ketorolactromethamine 5.0 parts
Benzalkonium chloride 6.0 parts All of these ingredients were added to toluene, adhesive base ingredients were dissolved and then applied on the mold-release paper at a thickness after dry of 100 μm. After dry, it was attached with polyester supports to afford the matrix-type percutaneously absorbable preparation of the invention.

Example 36

Styrene-isoprene-styrene block copolymer
(brand name: JSR SIS-5000) 35.0 parts
Acrylic adhesive
(brand name: Nissetsu AS-370) 47.0 parts
Ketorolactromethamine 10.0 parts
Ammonium chloride 8.0 parts Styrene-isoprene-styrene block copolymer, ketorolactromethamine and ammonium chloride were dissolved in an acrylic adhesive solution, and then applied on the mold-release paper at a thickness after dry of 50 μm. After dry, it was attached with polyester supports to afford the matrix-type percutaneously absorbable preparation of the invention.

Example 37

Polyisobutylene
(brand name: Opanol B-100) 20.0 parts
Acrylic adhesive
(brand name: DURO-TAK 87-2196) 56.0 parts
Ketorolactromethamine 20.0 parts
Diethylamine hydrochloride 4.0 parts Ketorolactromethamine and diethylamine hydrochloride were dissolved in an acrylic adhesive solution, to which a solution where polyisobutylene was dissolved in toluene was added, and mixed homogenously. Then, the solution was applied on the mold-release paper at a thickness after dry of 50 μm. After dry, it was attached with polyester supports to afford the matrix-type percutaneously absorbable preparation of the invention.

Example 38

Styrene-isoprene-styrene block copolymer
(brand name: cariflex TR-1107) 35.0 parts
Liquid paraffin 44.0 parts
Rosin resin
(brand name: KE-311) 15.0 parts
Sodium loxoprofene 2.0 parts
n-Dodecyl trimethyl ammonium chloride 4.0 parts All of these ingredients were added to toluene, adhesive base ingredients were dissolved and then applied on the mold-release paper at a thickness after dry of 100 μm. After dry, it was attached with polyester supports to afford the matrix-type percutaneously absorbable preparation of the invention.

Example 39

Acrylic adhesive
(brand name: Nissetsu KP-77) 55.0 parts
Sodium loxoprofene 25.0 parts
2-Ethylhexylamine hydrochloride 20.0 parts Sodium loxoprofene and diethylamine hydrochloride were dissolved in an acrylic adhesive solution, and then applied on the mold-release paper at a thickness after dry of 50 μm. After dry, it was attached with polyester supports to afford the matrix-type percutaneously absorbable preparation of the invention.

Example 40

Styrene-isoprene-styrene block copolymer
(brand name: Cariflex TR-1111) 10.0 parts Liquid paraffin 10.0 parts
Alicyclic saturated hydrocarbon resin
(brand name: Alcon P-100) 50.0 parts
Polyisobutylene
(brand name: Opanol B-100) 19.0 parts
Sodium loxoprofene 5.0 parts
Benzalkonium chloride 6.0 parts All of these ingredients were added to toluene, adhesive base ingredients were dissolved and then applied on the mold-release paper at a thickness after dry of 100 μm. After dry, it was attached with polyester supports to afford the matrix-type percutaneously absorbable preparation of the invention.

Example 41

Styrene-isoprene-styrene block copolymer
(brand name: JSR SIS-5000) 35.0 parts
Acrylic adhesive
(brand name: Nissetsu AS-370) 47.0 parts
Sodium loxoprofene 10.0 parts
Ammonium chloride 8.0 parts Styrene-isoprene-styrene block copolymer, sodium loxoprofene and ammonium chloride were dissolved in an acrylic adhesive solution, and then applied on the mold-release paper at a thickness after dry of 50 μm. After dry, it was attached with polyester supports to afford the matrix-type percutaneously absorbable preparation of the invention.

Example 42

Polyisobutylene
(brand name: Opanol B-100) 20.0 parts
Acrylic adhesive
(brand name: DURO-TAK 87-2196) 56.0 parts
Sodium loxoprofene 20.0 parts
Diethylamine hydrochloride 4.0 parts Sodium loxoprofene and diethylamine hydrochloride were dissolved in an acrylic adhesive solution, to which a solution where polyisobutylene was dissolved in toluene was added, and mixed homogenously. Then, the solution was applied on the mold-release paper at a thickness after dry of 50 μm. After dry, it was attached with polyester supports to afford the matrix-type percutaneously absorbable preparation of the invention.

Comparative Example 27

The patch was manufactured by way of trial by the same composition and process for production as those in Example 28, except that diethylamine hydrochloride which is the addition salt compound of the basic substance was not combined.

Comparative Example 28

The patch was manufactured by way of trial by the same composition and process for production as those in Example 29, except that diethylamine hydrochloride which is the addition salt compound of the basic substance was not combined.

Comparative Example 29

The patch was manufactured by way of trial by the same composition and process for production as those in Example 30, except that ammonium chloride which is the addition salt compound of the basic substance was not combined.

Comparative Example 30

The patch was manufactured by way of trial by the same composition and process for production as those in Example 31, except that ammonium chloride which is the addition salt compound of the basic substance was not combined.

Comparative Example 31

The patch was manufactured by way of trial by the same composition and process for production as those in Example 32, except that diethylamine hydrochloride which is the addition salt compound of the basic substance was not combined.

Comparative Example 32

The patch was manufactured by way of trial by the same composition and process for production as those in Example 33, except that n-dodecyl trimethyl ammonium chloride which is the addition salt compound of the basic substance was not combined.

Comparative Example 33

The patch was manufactured by way of trial by the same composition and process for production as those in Example 34, except that 2-ethylhexylamine hydrochloride which is the addition salt compound of the basic substance was not combined.

Comparative Example 34

The patch was manufactured by way of trial by the same composition and process for production as those in Example 35, except that benzalkonium chloride which is the addition salt compound of the basic substance was not combined.

Comparative Example 35

The patch was manufactured by way of trial by the same composition and process for production as those in Example 36, except that ammonium chloride which is the addition salt compound of the basic substance was not combined.

Comparative Example 36

The patch was manufactured by way of trial by the same composition and process for production as those in Example 37, except that diethylamine hydrochloride which is the addition salt compound of the basic substance was not combined.

Comparative Example 37

The patch was manufactured by way of trial by the same composition and process for production as those in Example 38, except that n-dodecyl trimethyl ammonium chloride which is the addition salt compound of the basic substance was not combined.

Comparative Example 38

The patch was manufactured by way of trial by the same composition and process for production as those in Example 39, except that 2-ethylhexylamine hydrochloride which is the addition salt compound of the basic substance was not combined.

Comparative Example 39

The patch was manufactured by way of trial by the same composition and process for production as those in Example 40, except that benzalkonium chloride which is the addition salt compound of the basic substance was not combined.

Comparative Example 40

The patch was manufactured by way of trial by the same composition and process for production as those in Example 41, except that ammonium chloride which is the addition salt compound of the basic substance was not combined.

Comparative Example 41

The patch was manufactured by way of trial by the same composition and process for production as those in Example 42, except that diethylamine hydrochloride which is the addition salt compound of the basic substance was not combined.

Test Example 2

In Vitro Skin Permeability Test

Pieces of dorsal skin in hairless mice (8 weeks of age, female) were excised and fat layers on the side of dermis were carefully removed. Water at 37° C. was set in a flow through cell which circulated periphery of a receptor layer such that the side of dermis became to be the receptor layer. The percutaneously absorbable preparation of the example or the comparative example was patched or applied on the side of a corneal layer, and phosphate buffer at pH 7.4 was used on the side of the receptor layer. Then sampling was done at a rate of 1 ml/h every one hour up to 24 hours. For the solution obtained every one hour, its quantity was accurately measured, and a concentration of a drug was determined by a high performance liquid chromatography method. A permeable rate per hour was calculated and a skin permeable rate in a steady state was determined according to the following formula.

Skin permeable rate ($\mu g/cm^2/hr$)=[Sample concentration ($\mu g/ml$)×Fluid flow (ml)]/Application area of preparation ($cm^2$)

The results are shown in Table 2.

TABLE 2

| | Skin permeable rate ($\mu g/cm^2/hr$) |
|---|---|
| Example 28 | 8.56 |
| Comparative Example 27 | 0.85 |
| Example 29 | 9.12 |
| Comparative Example 28 | 0.36 |
| Example 30 | 11.08 |
| Comparative Example 29 | 1.11 |
| Example 31 | 9.51 |
| Comparative Example 30 | 1.34 |
| Example 32 | 5.52 |
| Comparative Example 31 | 0.88 |
| Example 33 | 7.56 |
| Comparative Example 32 | 0.66 |
| Example 34 | 8.33 |

TABLE 2-continued

| | Skin permeable rate ($\mu g/cm^2/hr$) |
|---|---|
| Comparative Example 33 | 1.36 |
| Example 35 | 15.68 |
| Comparative Example 34 | 1.58 |
| Example 36 | 4.62 |
| Comparative Example 35 | 0.31 |
| Example 37 | 8.69 |
| Comparative Example 36 | 0.31 |
| Example 38 | 8.25 |
| Comparative Example 37 | 1.02 |
| Example 39 | 6.93 |
| Comparative Example 38 | 0.58 |
| Example 40 | 12.52 |
| Comparative Example 39 | 2.01 |
| Example 41 | 3.32 |
| Comparative Example 40 | 0.05 |
| Example 42 | 9.12 |
| Comparative Example 41 | 0.55 |

From the results of this test, it is shown that percutaneous absorption is remarkably increased in the percutaneously absorbable preparations containing the addition salt compound of the basic substance of the invention compared to those without the addition salt compound. When the acidic drug was used, and especially when the anti-inflammatory drug was used as the acidic drug, it is shown that excellent percutaneous absorption is observed even in the case containing it at high quantity of 25% by weight (see Examples 36 and 39).

INDUSTRIAL APPLICABILITY

As mentioned above, the invention provides the percutaneously absorbable preparation in which percutaneous absorbability of the acidic drug having salt-form is enhanced, and in particular the matrix-type percutaneously absorbable preparation in which percutaneous absorbability of the anti-inflammatory drug having salt-form is enhanced, without combining a special percutaneous absorption accelerator. The invention also provides a novel percutaneous absorption accelerating composition in which skin permeability and percutaneous absorbability of the acidic drug having salt-form can be remarkably improved by controlling multiple salts in a well-balanced manner.

Therefore, the percutaneously absorbable preparations of the invention can provide useful pharmaceutical preparations.

The invention claimed is:

1. A method for improving the percutaneous absorbability of sodium diclofenac in a non-aqueous patch comprising a matrix, the method comprising providing ammonium chloride in the patch at a range of from 0.5 to 10 fold mole/mole based on the sodium diclofenac.

2. The method according to claim 1, wherein ammonium chloride is blended at a range of from 0.5 to 7 fold mole/mole based on the sodium diclofenac.

3. The method according to claim 1, wherein the sodium diclofenac and the ammonium chloride are contained in an adhesive base layer.

4. The method according to claim 3, wherein the adhesive base layer is composed of one or more components selected from the group consisting of styrene-isoprene-styrene block copolymer, polyisobutylene, and acrylic adhesive.

* * * * *